US012616508B2

(12) United States Patent
Liang et al.

(10) Patent No.: US 12,616,508 B2
(45) Date of Patent: May 5, 2026

(54) ACROMIOCLAVICULAR STEEL PLATE ASSEMBLY HAVING JOINT FUNCTION

(71) Applicants: Junbo Liang, Taizhou (CN); Lie Lin, Taizhou (CN)

(72) Inventors: Junbo Liang, Taizhou (CN); Lie Lin, Taizhou (CN)

(73) Assignee: TAIZHOU ENZE MEDICAL CENTER, Taizhou (CN)

( * ) Notice: Subject to any disclaimer, the term of this patent is extended or adjusted under 35 U.S.C. 154(b) by 0 days.

(21) Appl. No.: 18/934,247

(22) Filed: Nov. 1, 2024

(65) Prior Publication Data

US 2026/0060727 A1 Mar. 5, 2026

(30) Foreign Application Priority Data

Aug. 28, 2024 (CN) .......................... 202411194259.4

(51) Int. Cl.
*A61B 17/80* (2006.01)

(52) U.S. Cl.
CPC ................................. *A61B 17/8061* (2013.01)

(58) Field of Classification Search
CPC .. A61B 17/80; A61B 17/8061; A61B 17/8076
See application file for complete search history.

(56) References Cited

U.S. PATENT DOCUMENTS 6,923,812 B1 * 8/2005 Wellisz ................ A61B 17/685
606/151
7,682,361 B2 * 3/2010 Knopfle ................ A61B 17/92
606/75
10,980,628 B2 4/2021 Wallace et al.
11,141,205 B2 10/2021 Cox
11,504,173 B2 * 11/2022 Seykora ............. A61B 17/8066
2006/0287654 A1 * 12/2006 Posnick ............... A61B 17/688
606/279
2020/0261117 A1 8/2020 Zenker et al.
2022/0022928 A1 1/2022 Cox

FOREIGN PATENT DOCUMENTS

CN 213129842 U 5/2021
CN 215778549 U 2/2022
WO 8201645 5/1982

* cited by examiner

*Primary Examiner* — Larry E Waggle, Jr.

(74) *Attorney, Agent, or Firm* — Minder Law Group; Willy H. Wong

(57) ABSTRACT

An acromioclavicular steel plate assembly includes an acromion steel plate and a clavicle steel plate, one end of the clavicle steel plate has a positioning head, the acromion steel plate is an integrated steel component with three perpendicular acromion planes in a U shape, the three acromion planes being a body, a first fixing portion, and a second fixing portion, a notch is arranged on a side surface of the first fixing portion, a first avoidance gap is provided in the body, two convex limiting protrusions and a convex spherical hinge protrusion are arranged on three side surfaces of the positioning head respectively, the positioning head can pass through the first avoidance gap and embed the spherical hinge protrusion into the notch, and a total width of the positioning head at the two limiting protrusions is greater than a width of the first avoidance gap.

11 Claims, 14 Drawing Sheets

ACROMIOCLAVICULAR STEEL PLATE ASSEMBLY HAVING JOINT FUNCTION

RELATED APPLICATIONS

This application claims priority to Chinese Patent Application No. 202411194259.4 filed Aug. 28, 2024.

The above applications and all patents, patent applications, articles, books, specifications, other publications, documents, and things referenced herein are hereby incorporated herein in their entirety for all purposes. To the extent of any inconsistency or conflict in the definition or use of a term between any of the incorporated publications, documents, or things and the text of the present document, the definition or use of the term in the present document shall prevail.

TECHNICAL FIELD

The disclosure belongs to the technical field of medical instruments, and relates to an acromioclavicular steel plate assembly.

BACKGROUND

An acromioclavicular joint, a component of a shoulder girdle of a human body, is a joint moving by nearly 20 degrees in all directions. Its stability is maintained primarily by ligaments. Dislocation of the acromioclavicular joint is clinically common. After injury to its ligamentous joint capsule, a distal end of a clavicle will probably be dislocated due to muscular pulling and the weight of the shoulder girdle. In view of this, a steel plate with a hook is widely used at home and abroad. It has the function of resisting upward dislocation of the distal end of the clavicle. However, since the hook is long and fixed, it is likely to scrape the lower acromion bone and even protrude into a shoulder joint during joint activities, resulting in bone injury and pain. Moreover, since the stability of the steel plate is insufficient, post-operation dislocation is still possible.

Another structure with an acromion steel plate attached to an acromion of a scapula is documented in the patent literature (e.g., Chinese patent with Publication No. CN213129842U), but clinical application of which is not found. The acromion steel plate is provided with a screw connected to the acromion of the scapula, a lower surface of the acromion steel plate is provided with a movable groove, a clavicle steel plate is connected to a clavicle, a distal end of the clavicle steel plate has a hemispherical connector, and the hemispherical connector is vertically embedded into the movable groove. Its mechanical principle is that the dislocation force of the clavicle acts on the clavicle steel plate, so the clavicle steel plate generates a force of prying off the acromion steel plate through the hemispherical connector, that is, the screw of the acromion steel plate is utilized to withstand dozens of pounds of upward tension. In real life, because the acromioclavicular joint moves by 20° in all directions, and the force of prying off the acromion steel plate is amplified, the screw is highly likely to be pulled out and fail. In addition, the positioning of the acromion steel plate on the acromion is typically inaccurate, causing the hemispherical connector to be pressed against the scapula when the acromioclavicular joint moves. As a result, frictional compression is generated between the hemispherical connector and the acromion of the scapula, and potential bone resorption and dislocation of the acromion steel plate are caused accordingly.

SUMMARY

An objective of the disclosure is to provide an acromioclavicular steel plate assembly in view of the above problems existing in the prior art. The technical problem to be solved by the disclosure is that an existing acromion steel plate is prone to dislocation in use.

The objective of the disclosure can be achieved by the following technical solution:

An acromioclavicular steel plate assembly includes an acromion steel plate and a strip-shaped clavicle steel plate, where one end of the clavicle steel plate has a positioning head, the acromion steel plate is an integrated steel component with three perpendicular acromion planes in a U shape, the three acromion planes being a body, a first fixing portion, and a second fixing portion, the first fixing portion being on a first end of the body and perpendicular to the body, the second fixing portion being on a second end of the body and perpendicular to the body, a notch is arranged on a side surface of the first fixing portion facing the second fixing portion, a first avoidance gap is provided in the body in a length direction of the body, two convex limiting protrusions are arranged on two side surfaces of the positioning head in a width direction of the clavicle steel plate respectively, a convex spherical hinge protrusion is arranged on one side surface of the positioning head in a thickness direction of the clavicle steel plate, the positioning head can pass through the first avoidance gap and embed the spherical hinge protrusion into the notch, and a total width W of the positioning head at the two limiting protrusions is greater than a width W0 of the first avoidance gap.

Working principle: when the acromion steel plate is connected to the clavicle steel plate, the positioning head is placed sideway (that is, the width direction of the clavicle steel plate is consistent with a length direction of a body of the acromion steel plate), then passes through the first avoidance gap of the body from one side of the body facing away from the first fixing portion, and rotates by 90 degrees after the limiting protrusions pass through the first avoidance gap (that is, the width direction of the clavicle steel plate is perpendicular to the length direction of the body of the acromion steel plate), and the spherical hinge protrusion of the positioning head faces the notch. Since the total width of the positioning head at the two limiting protrusions is greater than the width of the first avoidance gap, the limiting protrusions of the positioning head are blocked by the body, the positioning head slides along the first avoidance gap, then the spherical hinged protrusion is embedded into the notch, and hinge connection between the positioning head and the acromion steel plate is implemented. The clavicle steel plate is fixed at an outer end of a clavicle. The acromion steel plate is fixed on an acromion of a scapula, that is, the acromion is embedded into the U-shaped acromion steel plate. The second fixing portion is inserted below a lower bone surface of the acromion of the scapula and closely attached to the lower bone surface of the acromion. The first fixing portion is inserted above an upper bone surface of the acromion of the scapula. The first fixing portion is closely attached to the upper bone surface of the acromion and fixedly connected to the acromion. The body is located at a rear side of an acromioclavicular joint and closely attached to a bone at the acromion for limitation. When the bone fracture has occurred, the clavicle has upward thrust, the positioning head is tightly pressed on the first fixing portion of the acromion steel plate, and the acromion steel plate is fixed on the scapula, such that an upward pulling force of a distal end of the clavicle can be resisted. Hinged connection of the clavicle steel plate and the acromion steel plate is implemented by embedding the spherical hinge protrusion into the notch. A transverse limitation between the clavicle steel plate and the acromion steel plate is implemented through arrangement of the limiting protrusions. Therefore, not only the spherical hinge protrusion can always make contact and rotate with a wall surface of the notch when the acromioclavicular joint moves by 20° in all directions, such that the acromioclavicular joint can move normally and implement a normal acromioclavicular joint function; but also the acromion steel plate is located accurately on the acromion, and compression friction generated by the positioning head on the acromion is avoided. Furthermore, an upward dislocation force of the distal end of the clavicle is converted into pressure on the lower bone surface of the acromion of the scapula, and stable compression on the lower bone surface of the acromion by the second fixing portion of the U-shaped acromion steel plate is used, such that the acromion steel plate is fixed and stabilized on the acromion. Damage to the upper bone surface or the lower bone surface of the acromion caused by displacement of the acromion steel plate due to instability of fixation and caused by large transverse displacement of the positioning head is avoided, and a risk that screws are likely to be pulled off under the action of the dislocation force of the clavicle when the acromion steel plate is fixed on the upper bone surface of the acromion only by the screws is avoided. As shown above, use stability of the acromion steel plate and the acromioclavicular steel plate assembly is improved.

In one embodiment of the above acromioclavicular steel plate assembly, the two limiting protrusions are columnar, and two side surfaces of each of the two limiting protrusions in the thickness direction of the clavicle steel plate are cambered surfaces.

The shape of the limiting protrusions can guarantee structural strength of the limiting protrusions. The two side surfaces of each of the limiting protrusions are both cambered, such that friction between the positioning head and the scapula can be reduced after actual mounting, abrasion can be reduced when the acromioclavicular joint moves, and the use stability of the acromioclavicular steel plate assembly is improved.

In one embodiment of the above acromioclavicular steel plate assembly, the spherical hinge protrusion is hemispherical, and the two limiting protrusions are arranged close to middle of the spherical hinge protrusion or close to a side of the spherical hinge protrusion facing the body in a length direction of the clavicle steel plate.

With such arrangement, when the acromioclavicular joint moves, the spherical hinge protrusion and the limiting protrusions do not influence rotation of the scapula, and friction between the scapula and the clavicle steel plate is reduced.

In one embodiment of the above acromioclavicular steel plate assembly, a thickness H of the positioning head at the spherical hinge protrusion is less than a width W0 of the first avoidance gap. In this way, the positioning head may quickly penetrate the first avoidance gap, and convenience of mounting is guaranteed.

In one embodiment of the above acromioclavicular steel plate assembly, the clavicle steel plate is formed by three perpendicular clavicle planes in a Z shape, the three clavicle planes being the positioning head, a strip-shaped connecting portion capable of being connected to an upper bone surface on a clavicle, and an extending portion connected between the connecting portion and the positioning head, the extending portion and the connecting portion are perpendicularly arranged, and the extending portion and the spherical hinge protrusion are located on a same side surface of the positioning head.

The connecting portion is connected to the upper bone surface of the clavicle. When the clavicle has upward thrust, the clavicle has a tendency of pushing the connecting portion to move upwards. The extending portion is arranged perpendicular to the connecting portion, and the extending portion is configured to transmit a force, such that most of the upward thrust can be transmitted to the positioning head, the spherical hinge protrusion of the positioning head can be stably pressed in the notch, and the use stability of the acromioclavicular steel plate assembly is improved.

In one embodiment of the above acromioclavicular steel plate assembly, a width W2 of the body is less than a width W1 of the first fixing portion, the first avoidance gap penetrates the body in the length direction of the body, the second fixing portion is provided with a second avoidance gap in communication with the first avoidance gap, and the second avoidance gap penetrates the second fixing portion in the length direction of the body.

With such arrangement, the positioning head may quickly penetrate the first avoidance gap conveniently, and the width W2 of the body may be set less, which is advantageous to mounting of the acromion steel plate.

In one embodiment of the above acromioclavicular steel plate assembly, one side surface of the connecting portion in the width direction of the clavicle steel plate has a convex connection reinforcing portion, and the connection reinforcing portion is provided with a reinforcing hole.

A plurality of connecting holes are provided in the connecting portion, and the connecting portion and the connection reinforcing portion of the clavicle steel plate are fixedly connected to the upper bone surface of the clavicle through screws. The arrangement of the connection reinforcing portion not only improves structural strength of the clavicle steel plate, but also improves strength of connection between the clavicle steel plate and the clavicle.

In one embodiment of the above acromioclavicular steel plate assembly, each of the two limiting protrusions is symmetrically arranged in a radial direction of the spherical hinge protrusion.

With such arrangement, the limiting protrusions can implement limiting without influencing movement of the spherical hinge protrusion, such that the acromioclavicular joint is guaranteed to have a movable space of 20° in all directions.

In one embodiment of the above acromioclavicular steel plate assembly, the first fixing portion has a plurality of first fixing holes and one second fixing hole. The first fixing portion may be connected to the upper bone surface of the scapula through the first fixing holes by screws. The second fixing portion has a third fixing hole arranged corresponding to the second fixing hole. The first fixing portion and the second fixing portion are connected by making a reinforcing screw penetrate the second fixing hole and the third fixing hole sequentially.

The third fixing hole is a threaded hole. The first fixing portion and the second fixing portion are connected by making the reinforcing screw penetrate the second fixing hole and the third fixing hole sequentially, such that connection between the second fixing portion and the first fixing portion is more stable. The second fixing portion may stably be attached to the lower bone surface of the scapula, and the stability of fixed connection between the acromion steel plate and the scapula is improved.

In one embodiment of the above acromioclavicular steel plate assembly, the second fixing hole is arranged closer to middle of the first fixing portion than the first fixing hole.

With the arrangement of the position of the second fixing hole, the connection between the first fixing portion and the second fixing portion is located in the middle portion. Strength of the middle portion is higher, and stress in the middle portion is more stable, such that the stability of the connection between the second fixing portion and the first fixing portion is improved.

In another embodiment, an acromioclavicular steel plate assembly includes an acromion steel plate and a strip-shaped clavicle steel plate, where one end of the clavicle steel plate has a positioning head, the acromion steel plate is an integrated steel component with three perpendicular acromion planes in a U shape, the three acromion planes being a body, a first fixing portion, and a second fixing portion, the first fixing portion being on a first end of the body and perpendicular to the body, the second fixing portion being on a second end of the body and perpendicular to the body, a bottom notch and two limiting hooks that are distributed in a width direction of the body are arranged on a side surface of the second fixing portion facing away from the first fixing portion, an avoidance clearance is formed between the two limiting hooks, two convex limiting protrusions are arranged on two side surfaces of the positioning head in a width direction of the clavicle steel plate respectively, a convex spherical hinge protrusion is arranged on one side surface of the positioning head in a thickness direction of the clavicle steel plate, the positioning head is capable of passing through the avoidance clearance and embedding the spherical hinge protrusion into the bottom notch, and a total width W of the positioning head at the two limiting protrusions is greater than a width W3 of the avoidance clearance.

In one embodiment of the above acromioclavicular steel plate assembly, each of the two limiting hooks is in a shape of an obtuse degree angled line, and includes a limitation supporting portion arranged obliquely and a limitation reinforcing portion parallel to the second fixing portion.

With such arrangement, internal muscles in the scapula and other portions are avoided, and positioning of the limiting hooks is facilitated.

In one embodiment of the above acromioclavicular steel plate assembly, an avoidance space allowing the positioning head to rotate is provided between the limitation reinforcing portion and the second fixing portion.

The arrangement of positions of the limiting hooks improves stability of the limiting hooks, and the limiting hooks do not influence the rotation of the positioning head through the avoidance space, such that a normal function of the acromioclavicular joint can be implemented after the acromioclavicular steel plate assembly is mounted.

Compared with the prior art, the disclosure has the following advantages:

1. According to one embodiment of the acromioclavicular steel plate assembly, the acromioclavicular joint can move normally, damage to the upper bone surface or the lower bone surface of the acromion caused by displacement of the acromion steel plate due to instability of fixation and caused by large transverse displacement of the positioning head is avoided, a risk that screws are likely to be pulled off under the action of the dislocation force of the clavicle when the acromion steel plate is fixed on the upper bone surface of the acromion only by the screws is avoided, and the use stability of the acromioclavicular steel plate assembly is improved.

2. The extending portion of the clavicle steel plate is configured to transmit a force, and can transmit most of the upward thrust borne by the connecting portion to the positioning head, such that the spherical hinge protrusion of the positioning head can be stably pressed in the notch or the bottom notch, and the use stability of the acromioclavicular steel plate assembly can be improved.

DETAILED DESCRIPTION

Set forth below are specific embodiments of the present disclosure and a further description of the technical solutions of the present disclosure in conjunction with the accompanying drawings, but the present disclosure is not limited to these embodiments.

Embodiment I

Figure 1:
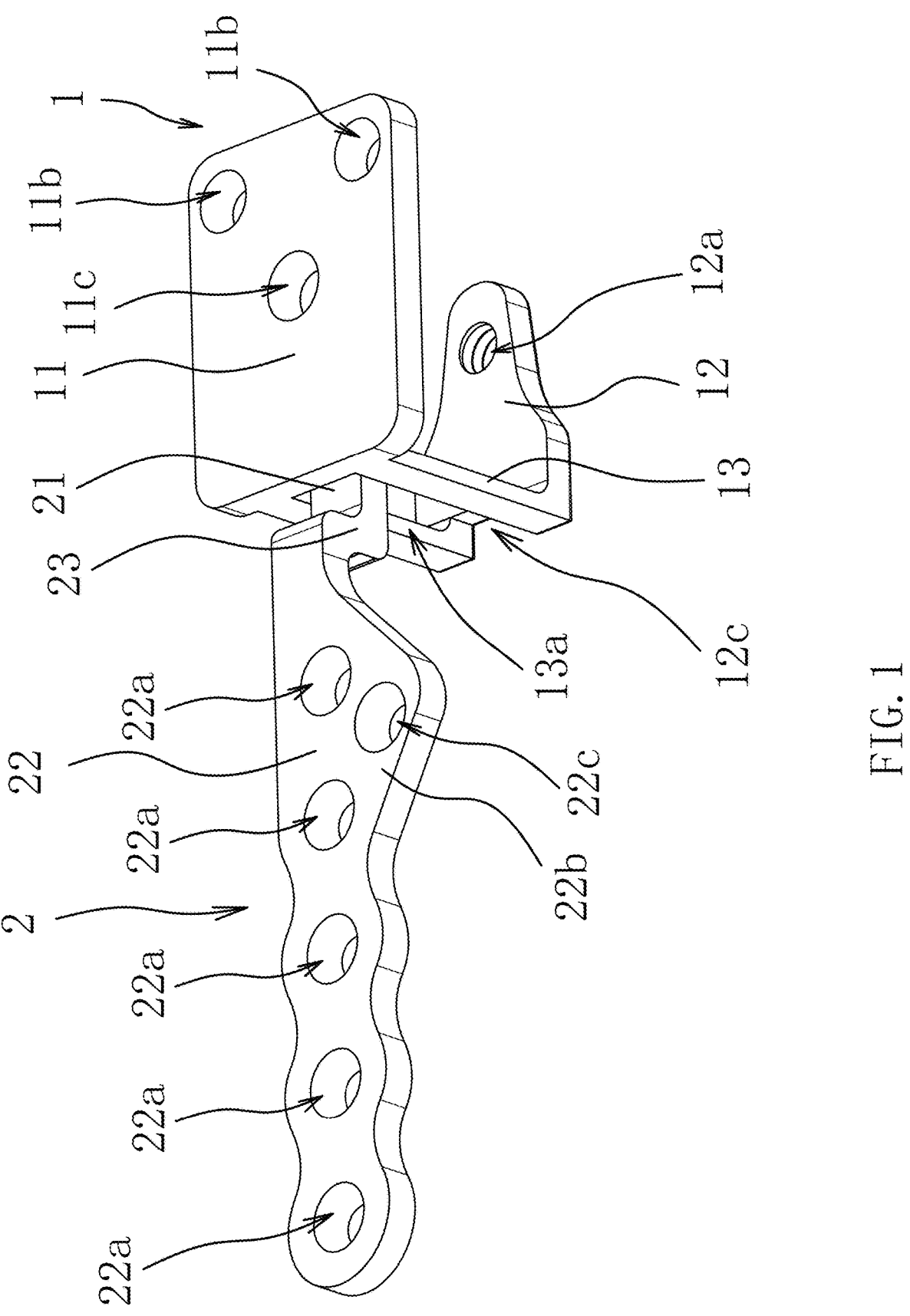
FIG. 1 is a first perspective view showing a schematic structure of Embodiment I of an acromioclavicular steel plate assembly.
Figure 2:
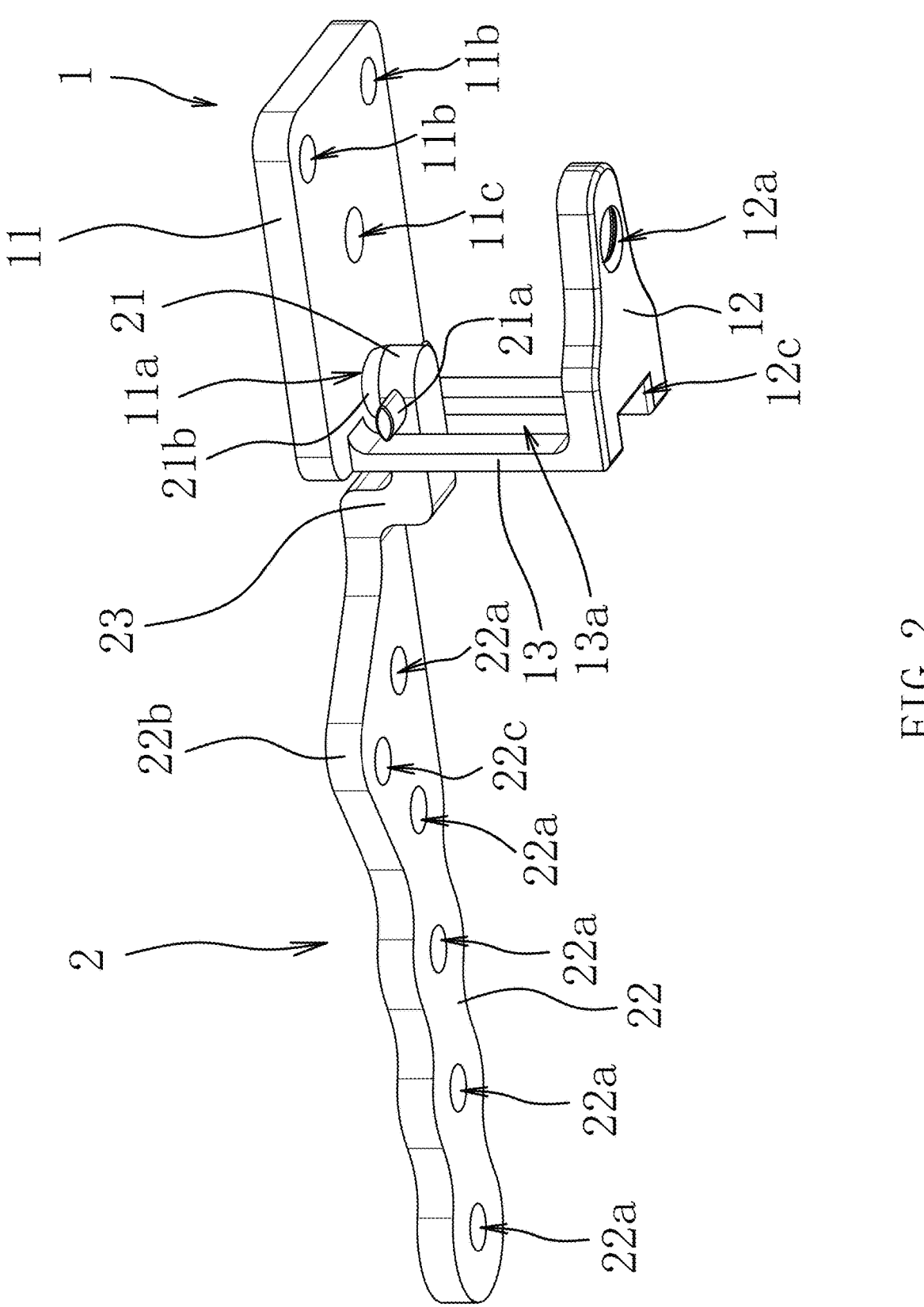
FIG. 2 is a second perspective view showing a schematic structure of Embodiment I of an acromioclavicular steel plate assembly, from another viewing angle.
Figure 5:
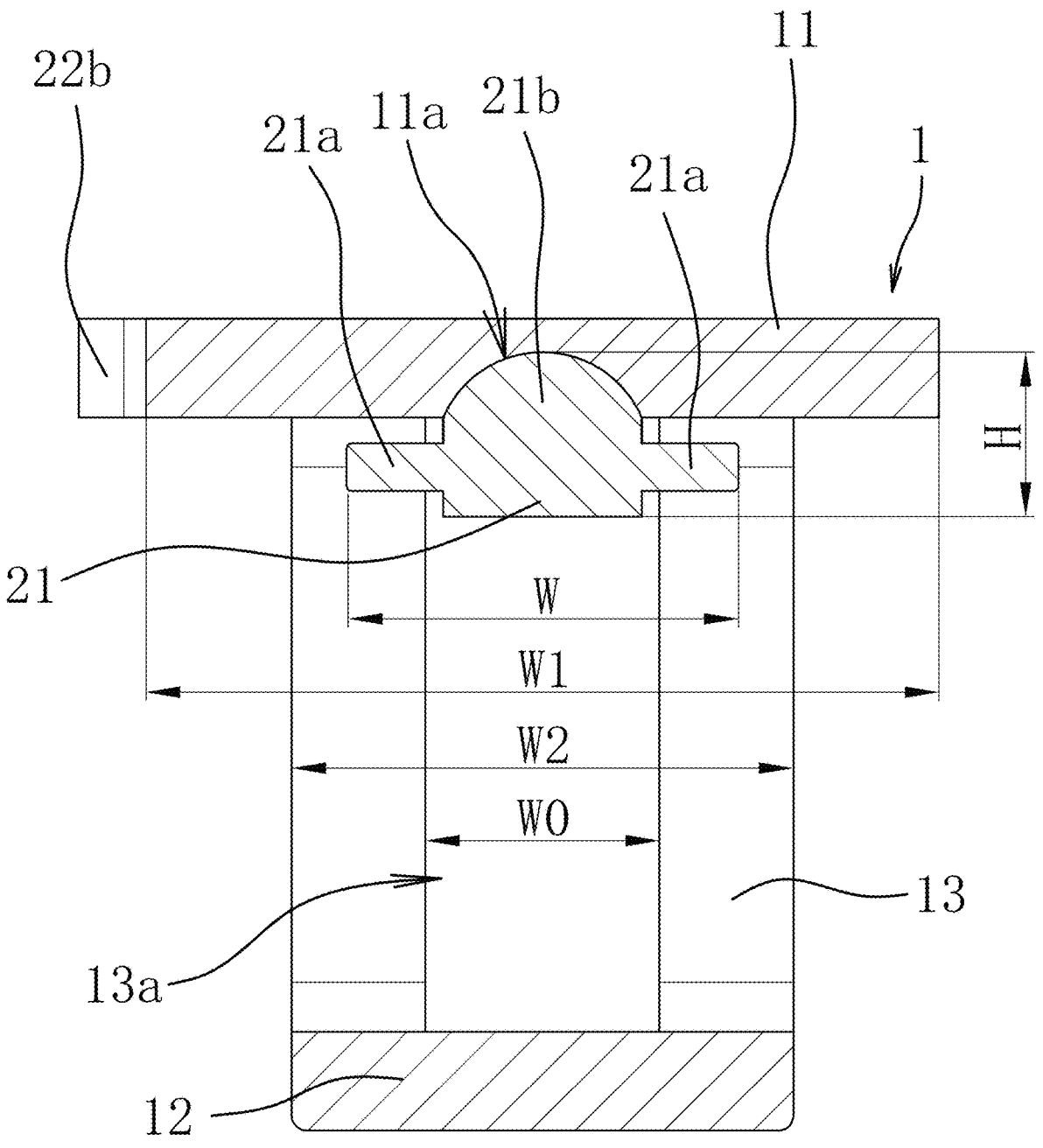
FIG. 5 is a sectional view in direction A-A in FIG. 4 (rotated clockwise by 90°)

As shown in FIGS. 1 and 2, an acromioclavicular steel plate assembly includes an acromion steel plate 1 and a clavicle steel plate 2. One end of the clavicle steel plate 2 has a positioning head 21. The clavicle steel plate 2 is formed by three perpendicular clavicle planes in a Z shape, the three clavicle planes being the positioning head 21, a strip-shaped connecting portion 22 for being connected to an upper bone surface on a clavicle 3, and an extending portion 23 connected between the connecting portion 22 and the positioning head 21. The acromion steel plate 1 is an integrated steel component with three perpendicular acromion planes in a U shape, the three acromion planes being a body 13, a first fixing portion 11, and a second fixing portion 12, the first fixing portion 11 being on a first end of the body 13 and perpendicular to the body 13, the second fixing portion 12 being on a second end of the body 13 and perpendicular to the body 13. A first avoidance gap 13a is provided in the body 13 in a length direction of the body 13. In conjunction with FIG. 7, two convex limiting protrusions 21a are arranged on two side surfaces of the positioning head 21 in a width direction of the clavicle steel plate 2 respectively. A convex spherical hinge protrusion 21b is arranged on one side surface of the positioning head 21 in a thickness direction of the clavicle steel plate 2. The spherical hinge protrusion 21b has a spherical limiting surface 21b1. In conjunction with FIG. 6, a notch 11a is arranged on a side surface of the first fixing portion 11 facing the second fixing portion 12. The notch 11a is arranged close to the body 13. A wall surface of the notch 11a has a spherical shape and matches the spherical limiting surface 21b1. The positioning head 21 can pass through the first avoidance gap 13a and insert the spherical hinge protrusion 21b into the notch 11a. As shown in FIG. 5, a total width W of the positioning head 21 at the two limiting protrusions 21a is greater than a width W0 of the first avoidance gap 13a.

Figure 3:
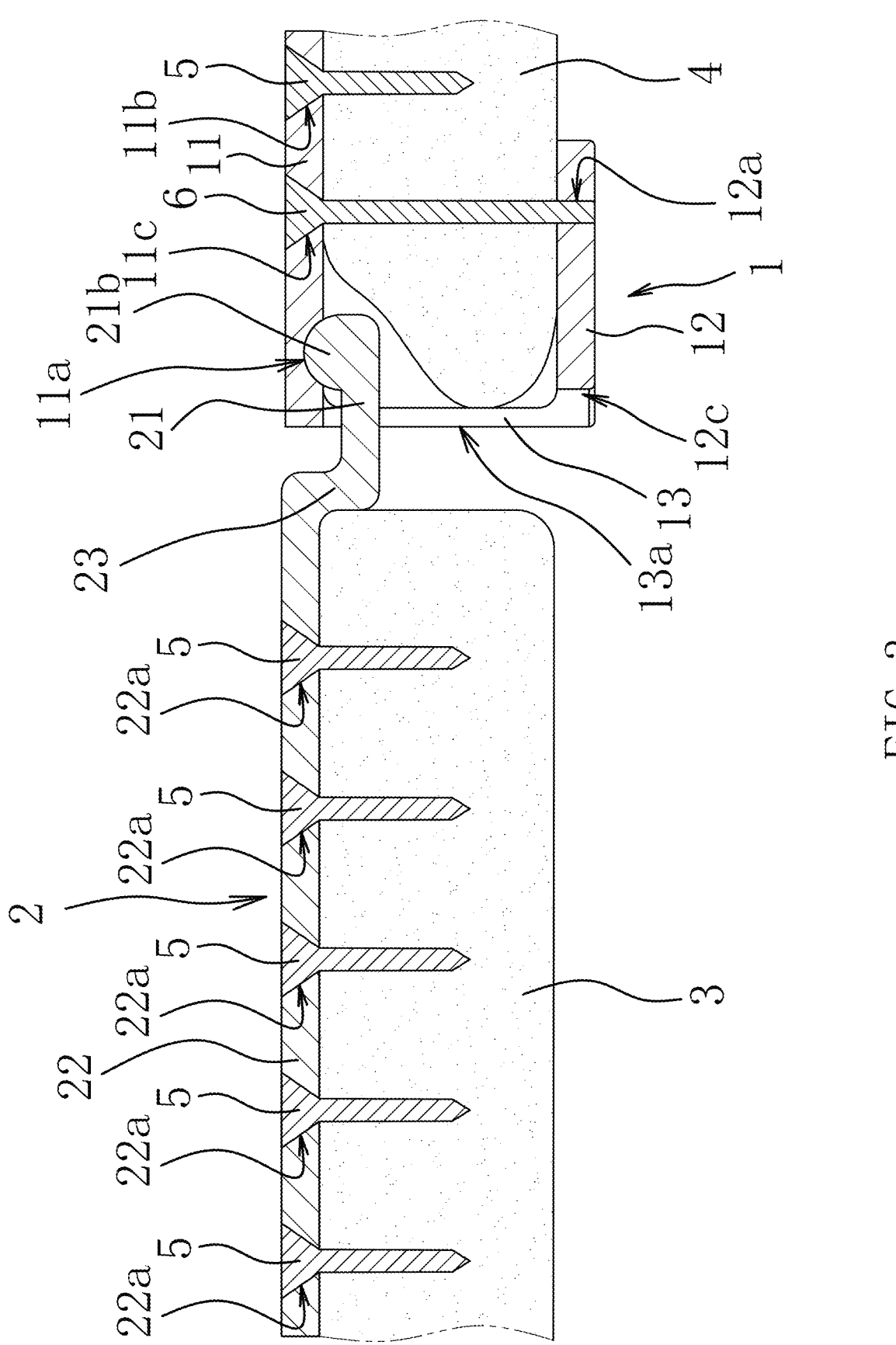
FIG. 3 is a sectional view showing a schematic structure of Embodiment I of an acromioclavicular steel plate assembly after mounting.
Figure 7:
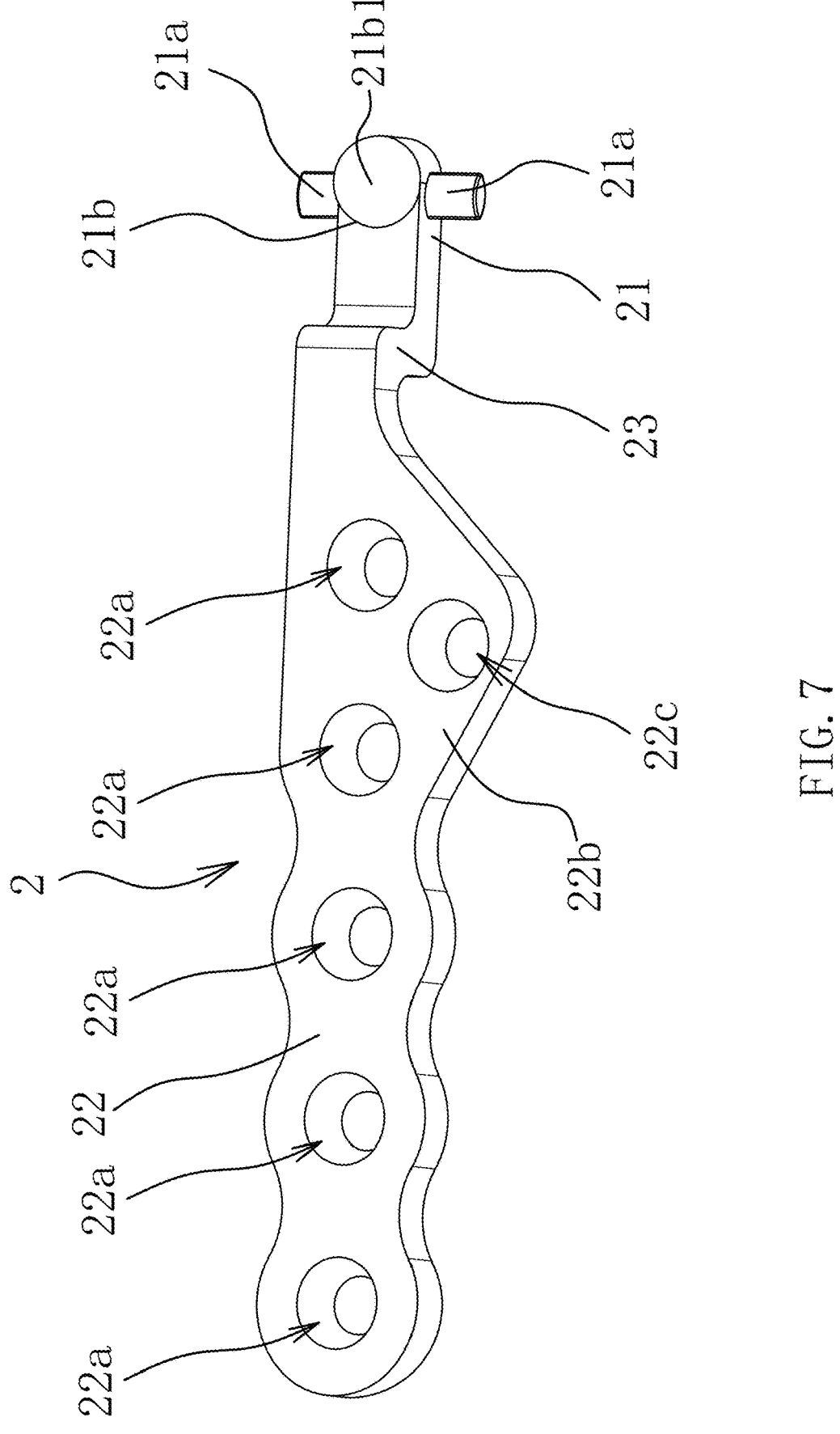
FIG. 7 is a perspective view showing a schematic structure of a clavicle steel plate of Embodiment I of an acromioclavicular steel plate assembly.

As shown in FIGS. 2, 3 and 7, the extending portion 23 and the connecting portion 22 are perpendicularly arranged, and the extending portion 23 and the spherical hinge protrusion 21b are located on a same side surface of the positioning head 21. The connecting portion 22 has a connection reinforcing portion 22b convex forwards. Five connecting holes 22a are provided in the connecting portion 22. A reinforcing hole 22c is provided in the connection reinforcing portion 22b. The extending portion 23 and the positioning head 21 are formed by bending, that is, the connecting portion 22, the extending portion 23 and the positioning head 21 of the clavicle steel plate 2 are integrally formed by using a plate, such that the clavicle steel plate 2 has greater stability.

An anteroposterior direction refers to an anteroposterior direction of a human body. When the acromion steel plate 1 is connected to the clavicle steel plate 2, the first fixing portion 11 of the acromion steel plate 1 is placed horizontally and upwards, the clavicle steel plate 2 is placed sideway, and the spherical hinge protrusion 21b on the positioning head 21 may be arranged forwards or backwards. Then, the positioning head 21 transversely passes through the first avoidance gap 13a of the body 13 from a side of the body 13 facing away from the first fixing portion 11. After the limiting protrusions 21a crosses the first avoidance gap 13a, the clavicle steel plate 2 rotates by 90 degrees to make the spherical hinge protrusion 21b face the notch 11a. The limiting protrusions 21a of the positioning head 21 are blocked and limited transversely by the body 13. The positioning head 21 slides vertically, and then the spherical hinge protrusion 21b is embedded into the notch 11a vertically upwards, such that hinged connection and transverse limitation between the positioning head 21 and the acromion steel plate 1 is implemented. After the spherical hinge protrusion 21b is embedded into the notch 11a, there are movable gaps between the extending portion 23 and the body 13, between the positioning head 21 and a sidewall of the first avoidance gap 13a, between the positioning head 21 and the first fixing portion 11, and between the limiting protrusions 21a and the body 12. The movable gaps do not need to be too large, so as to adapt to a movable range of 20° in all directions between the acromion steel plate 1 and the clavicle steel plate 2 for avoiding interference.

Figure 4:
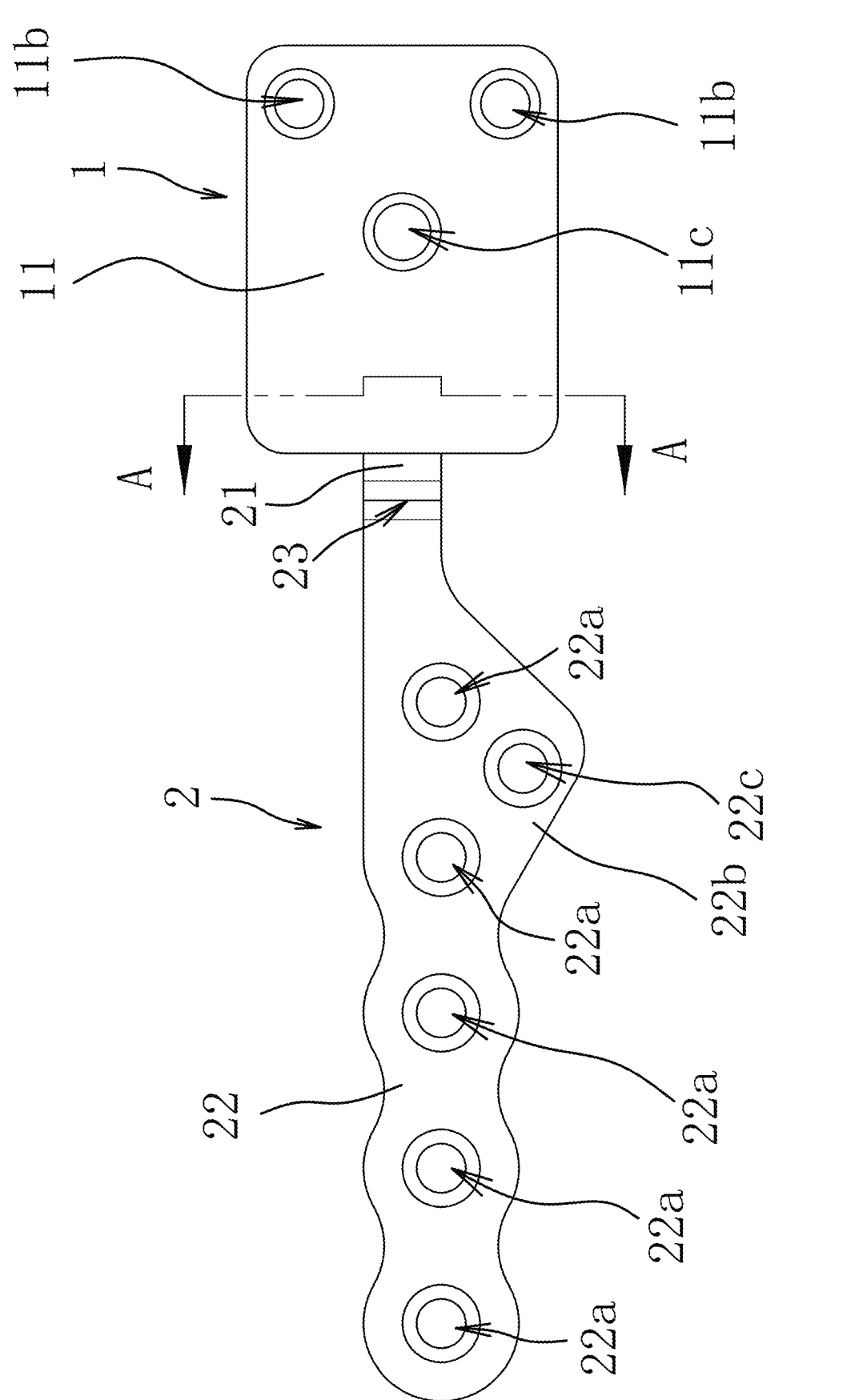
FIG. 4 is a top view of Embodiment I of an acromioclavicular steel plate assembly.

As shown in FIGS. 2, 3 and 4, the first fixing portion 11 has two first fixing holes 11b allowing the screws 5 to penetrate and one second fixing hole 11c allowing the reinforcing screw 6 to penetrate. The second fixing portion 12 has a third fixing hole 12a arranged corresponding to the second fixing hole 11c. The third fixing hole 12a is a threaded hole. The third fixing hole 12a may establish a threaded connection with the reinforcing screw 6. The first fixing portion 11 may be connected to the upper bone surface of the acromion 4 of the scapula through the first fixing hole 11b by the screws 5. The first fixing portion 11 and the second fixing portion 12 are connected through the second fixing hole 11c and the third fixing hole 12a by the reinforcing screws 6 sequentially. The two first fixing holes 11b are located at corners of one end of the first fixing portion 11 away from the body 13 respectively. The second fixing hole 11c is arranged closer to the middle of the first fixing portion 11 than the first fixing hole 11b.

Figure 6:
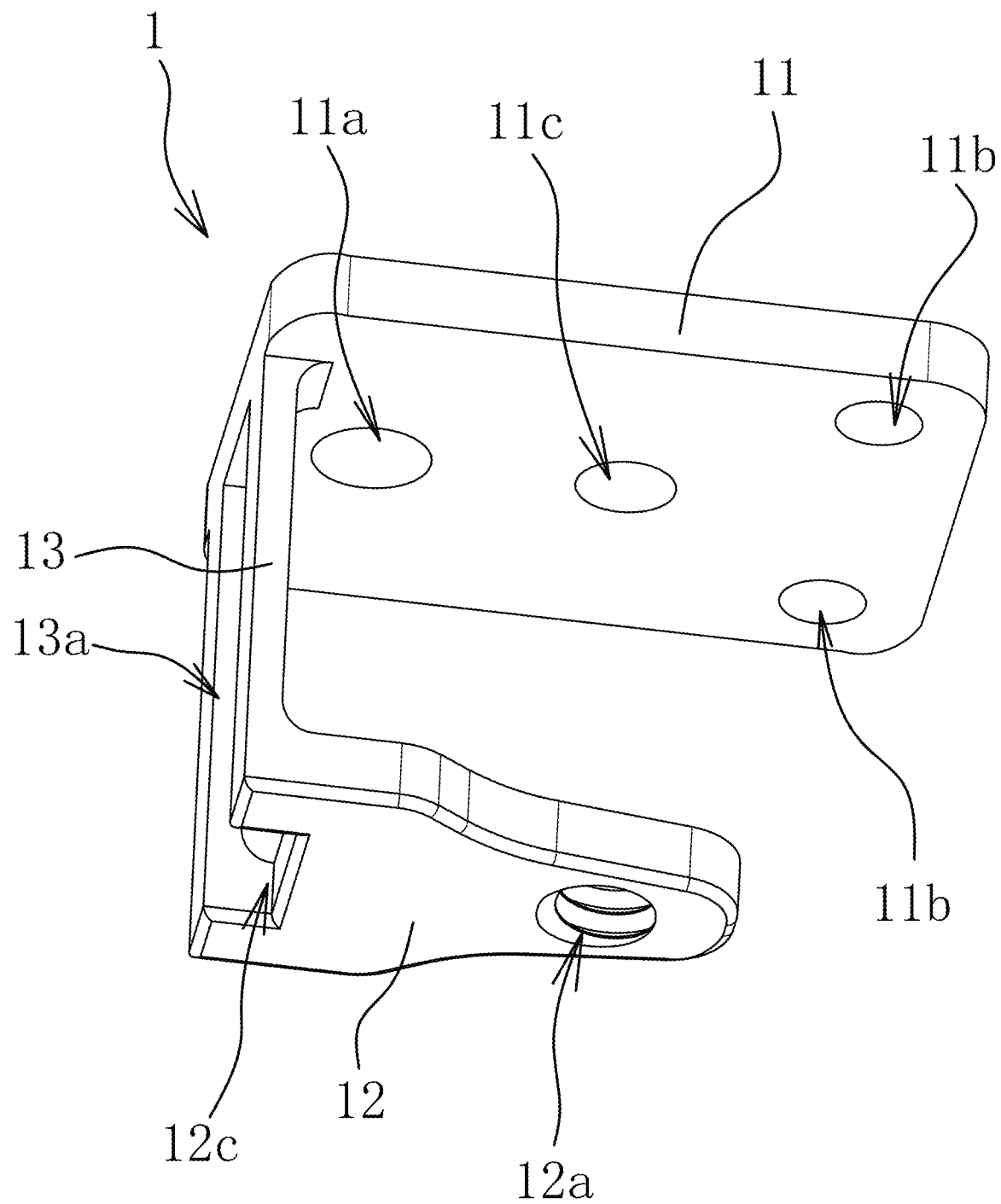
FIG. 6 is a perspective view showing a schematic structure of an acromion steel plate of Embodiment I of an acromioclavicular steel plate assembly.

As shown in FIGS. 5 and 6, a width W2 of the body 13 is less than a width W1 of the first fixing portion 11. The first avoidance gap 13a penetrates the body 13 in the length direction of the body 13. The second fixing portion 12 is provided with a second avoidance gap 12c in communication with the first avoidance gap 13a. The second avoidance gap 12c penetrates the second fixing portion 12 in the length direction of the body 13.

As shown in FIGS. 2, 5 and 7, each of the two limiting protrusions 21a is columnar, and two side surfaces of each of the two limiting protrusions 21a in the thickness direction of the clavicle steel plate 2 are cambered surfaces. The spherical hinge protrusion 21b is hemispherical. The limiting protrusions 21a are arranged close to the middle of the spherical hinge protrusion 21b or close to a side of the spherical hinge protrusion 21b facing the body 13 in a length direction of the clavicle steel plate 2. Each of the two limiting protrusions 21a is symmetrically arranged in a radial direction of the spherical hinge protrusion 21b. A thickness H of the positioning head 21 at the spherical hinge protrusions 21b is less than the width W0 of the first avoidance gap 13a.

As shown in FIG. 3, the clavicle steel late 2 is fixed on the upper bone surface of the distal end of the clavicle 3 with six screws 5. The acromion steel plate 1 is fixed on the acromion 4 of the scapula with two screws 5 and one reinforcing screw 6, that is to say, the acromion 4 is embedded into the U-shaped acromion steel plate 1, and the first fixing portion 11 and the second fixing portion 12 are inserted above and below the acromion 4 respectively. The first fixing portion 11 is closely attached to the upper bone surface of the acromion 4, the second fixing portion 12 is closely attached to the lower bone surface of the acromion 4, and the body 13 is located at a rear side of the acromioclavicular joint and closely abuts against the bone at the acromion 4 for limitation, such that the clavicle steel plate 2 is accurately mounted and located on the acromion 4. One reinforcing screw 6 penetrates the second fixing hole 11c of the first fixing portion 11 and the acromion 4 and then is in screwed connection to the third fixing hole 12a of the second fixing portion 12. The first fixing portion 11 is closely attached to the upper bone surface of the acromion 4 and is fastened and fixed to the second fixing portion 12 through the reinforcing screw 6. Two screws 5 penetrate the two first fixing holes 11*b* respectively and then are fixedly connected to the acromion 4. The hinged connection between the clavicle steel plate 2 and the acromion steel plate 1 is implemented by embedding the spherical hinge protrusion 21*b* into the notch 11*a*. The transverse limitation between the clavicle steel plate 2 and the acromion steel plate 1 is implemented by arranging the limiting protrusions 21*a*, that is to say, a transverse movement range of the positioning head 21 is limited, and the positioning head 21 is guaranteed not to be dislocated from the first avoidance gap 13*a* of the body 13 when the acromioclavicular steel plate assembly is in use.

When the acromioclavicular joint moves by 20° in all directions after the acromioclavicular steel plate assembly is mounted, the spherical hinge protrusion 21*b* can always make contact with the wall surface of the notch 11*a* and rotate, such that the acromioclavicular joint can move normally and implement a normal acromioclavicular joint function. When bone fracture has occurred, the clavicle 3 has upward thrust, the positioning head 21 is tightly pressed on the acromion steel plate 1, that is, the spherical hinge protrusion 21*b* presses the wall surface of the notch 11*a*, and the acromion steel plate 1 is fixed on the acromion 4, such that an upward pulling force of a distal end of the clavicle 3 can be resisted. Furthermore, an upward dislocation force of the distal end of the clavicle 3 is converted into pressure on the lower bone surface of the acromion 4 of the scapula, and stable compression on the lower bone surface of the acromion 4 by the second fixing portion 12 of the U-shaped acromion steel plate 1 is used, such that damage to the upper bone surface or the lower bone surface of the acromion 4 caused by displacement of the acromion steel plate 1 due to instability of fixation and caused by large transverse displacement of the positioning head 21 is avoided, a risk that screws 5 are likely to be pulled off under the action of the dislocation force of the clavicle 3 when the acromion steel plate 1 only having the first fixing portion 11 is fixed on the upper bone surface of the acromion 4 only by the screws 5 is avoided, and use stability of the acromioclavicular steel plate assembly is improved.

Embodiment II

Figure 8:
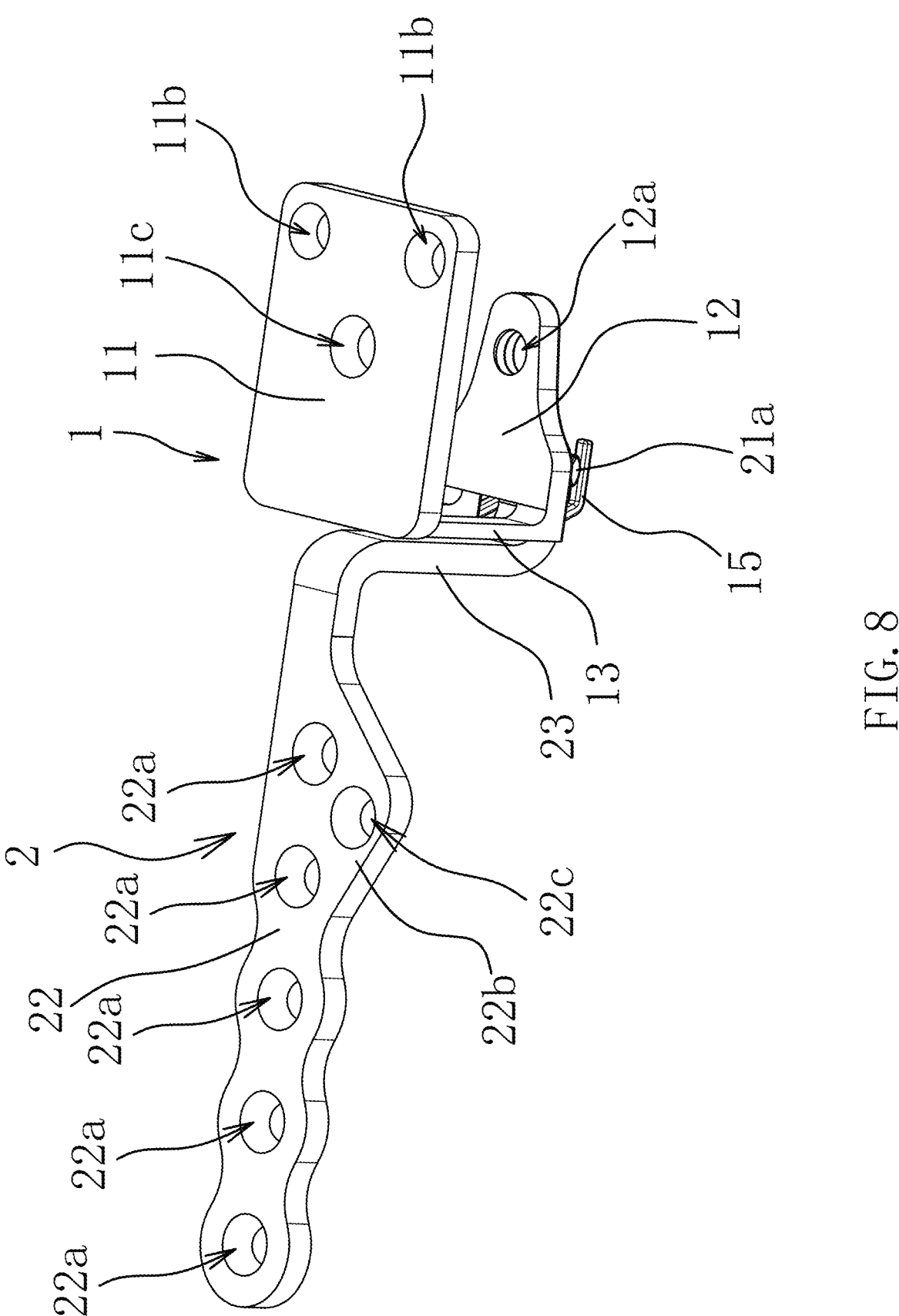
FIG. 8 is a first perspective view showing a schematic structure of Embodiment II of an acromioclavicular steel plate assembly.
Figure 9:
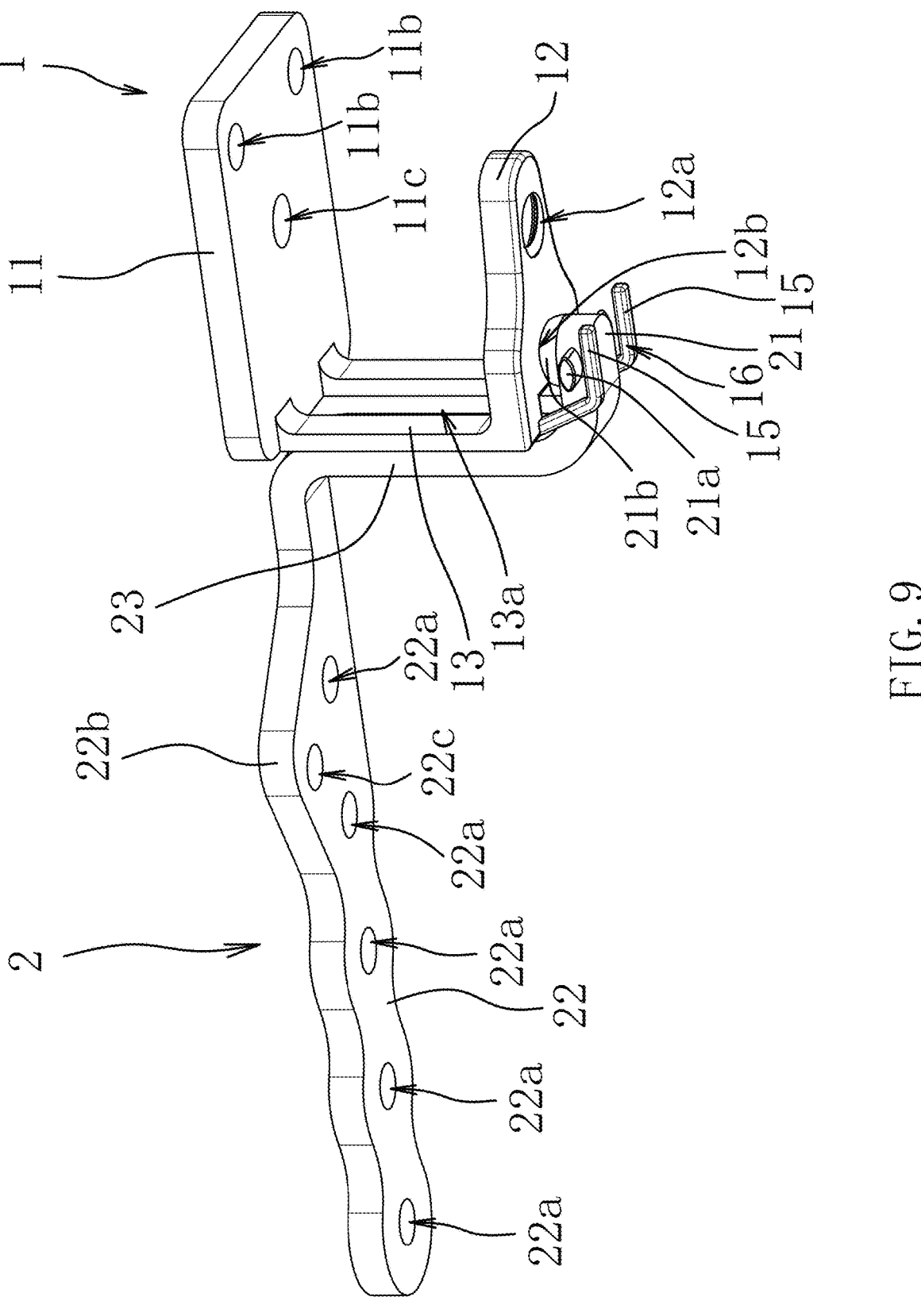
FIG. 9 is a second perspective view showing a schematic structure of Embodiment II of an acromioclavicular steel plate assembly, from another viewing angle.
Figure 12:
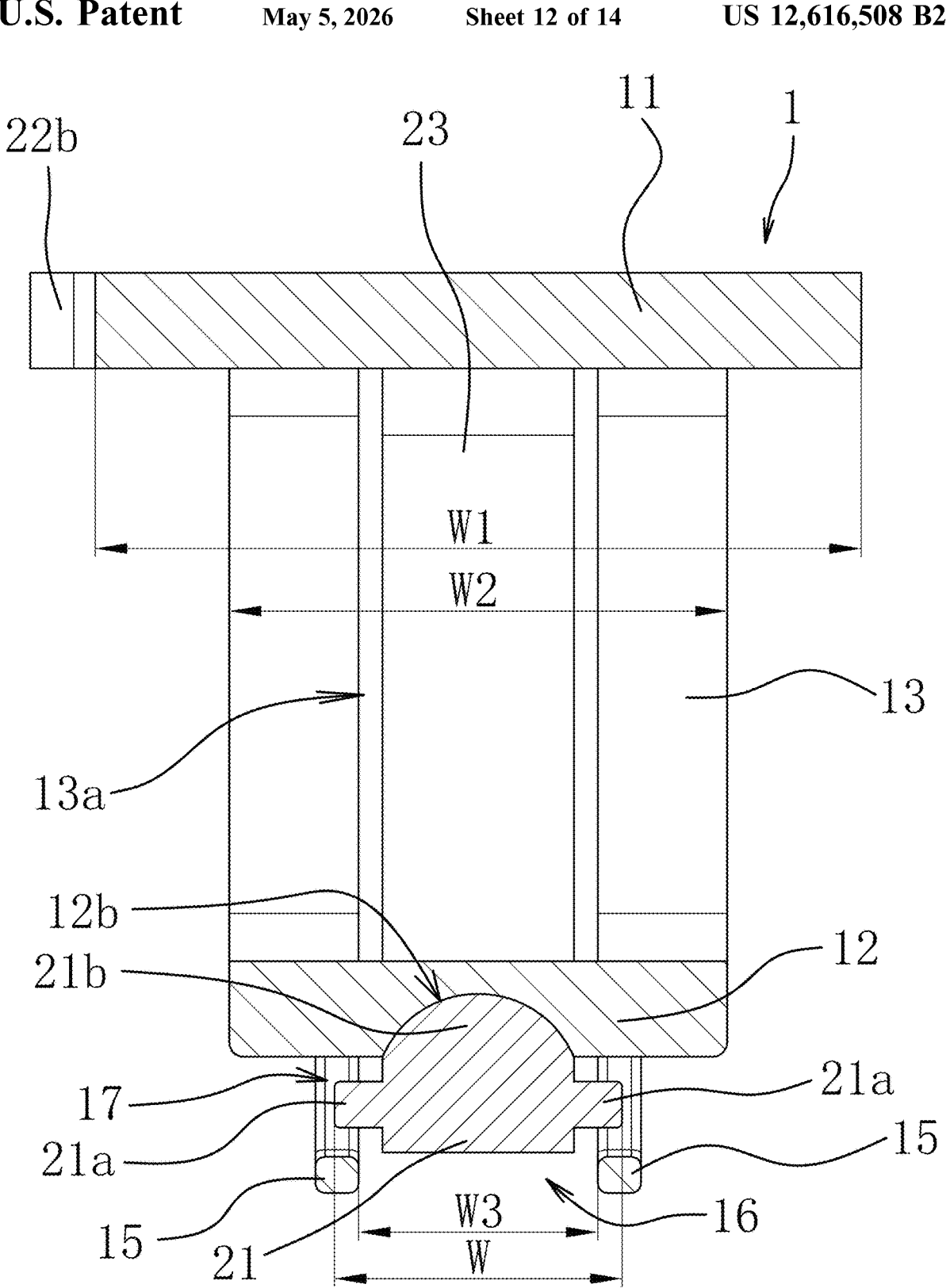
FIG. 12 is a sectional view in direction b-b in FIG. 11 (rotated clockwise by 90°)

As shown in FIGS. 8 and 9, another acromioclavicular steel plate assembly includes an acromion steel plate 1 and a clavicle steel plate 2. One end of the clavicle steel plate 2 has a positioning head 21. The clavicle steel plate 2 is formed by three perpendicular clavicle planes in a Z shape, the three clavicle planes being the positioning head 21, a strip-shaped connecting portion 22 for being connected to an upper bone surface on a clavicle 3, and an extending portion 23 connected between the connecting portion 22 and the positioning head 21. The acromion steel plate 1 is an integrated steel component with three perpendicular acromion planes in a U shape, the three acromion planes being a body 13, a first fixing portion 11, and a second fixing portion 12, the first fixing portion 11 being on a first end of the body 13 and perpendicular to the body 13, the second fixing portion 12 being on a second end of the body 13 and perpendicular to the body 13. In conjunction with FIG. 13, the second fixing portion 12 has two limiting hooks 15 distributed in a width direction of the body 13. An avoidance clearance 16 is formed between the two limiting hooks 15. Each of the two limiting hooks 15 is in a shape of an obtuse degree angled line, and includes a limitation supporting portion 15*a* arranged obliquely and a limitation reinforcing portion 15*b* parallel to the second fixing portion 12. The angle between the limitation supporting portion 15*a* and the limitation reinforcing portion 15*b* can be 100°~150°, such as 110° or 120°. An avoidance space 17 allowing the positioning head 21 to rotate is provided between the limitation reinforcing portion 15*b* and the second fixing portion 12. In conjunction with FIG. 14, two convex limiting protrusions 21*a* are arranged on two side surfaces of the positioning head 21 in a width direction of the clavicle steel plate 2 respectively. A convex spherical hinge protrusion 21*b* is arranged on one side surface of the positioning head 21 in a thickness direction of the clavicle steel plate 2. The spherical hinge protrusion 21*b* has a spherical limiting surface 21*b*1. In conjunction with FIG. 13, a bottom notch 12*b* is arranged on a side surface of the second fixing portion 12 facing the first fixing portion 1. The bottom notch 12*b* is arranged close to the body 13. A wall surface of the bottom notch 12*b* has a spherical shape and matches the spherical limiting surface 21*b*1. The positioning head 21 can pass through the avoidance clearance 16 and insert the spherical hinge protrusion 21*b* into the bottom notch 12*b*. As shown in FIG. 12, a total width W of the positioning head 21 at the two limiting protrusions 21*a* is greater than a width W3 of the avoidance clearance 16.

Figure 10:
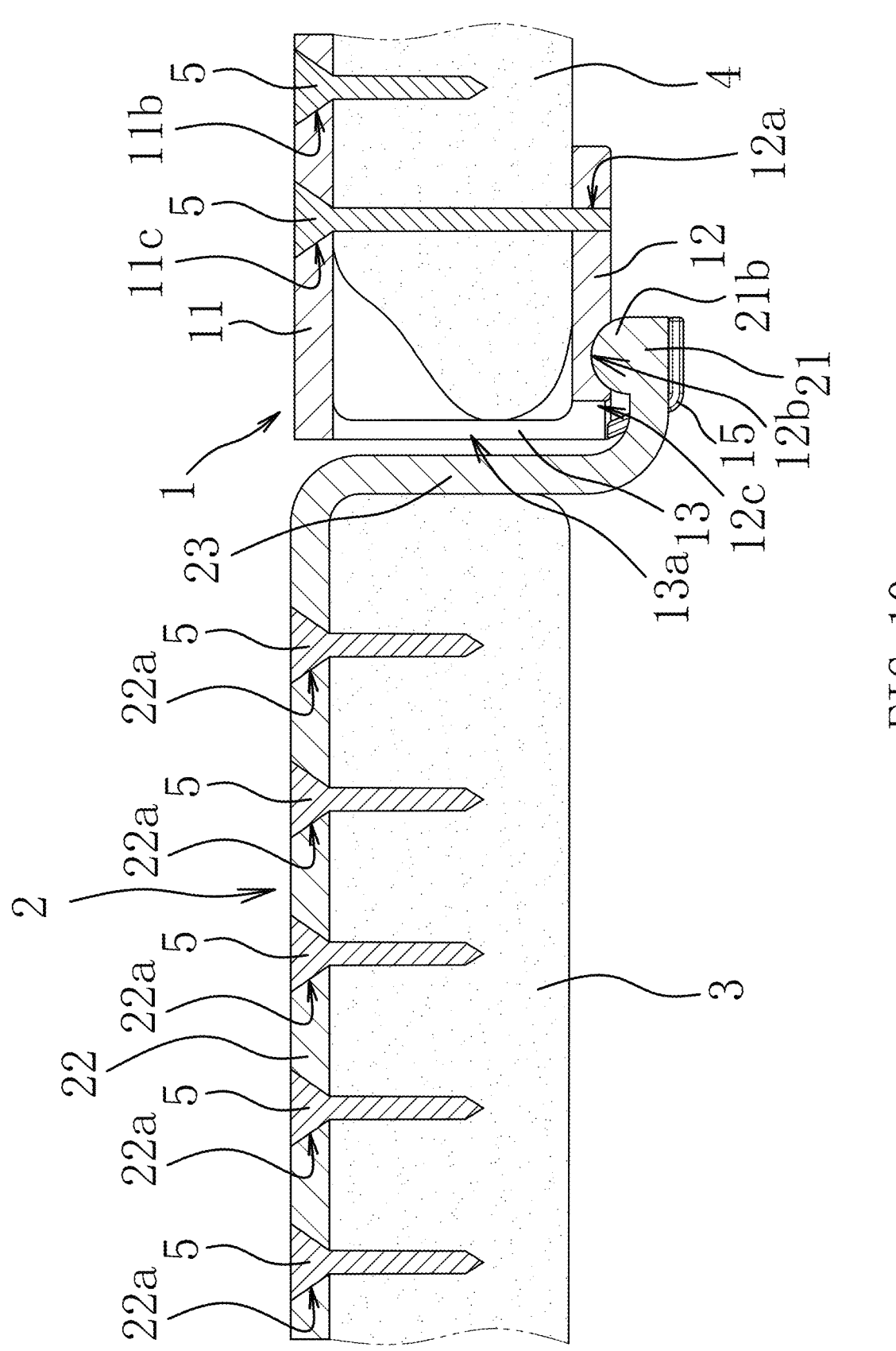
FIG. 10 is a sectional view showing a schematic structure of Embodiment II of an acromioclavicular steel plate assembly after mounting.
Figure 11:
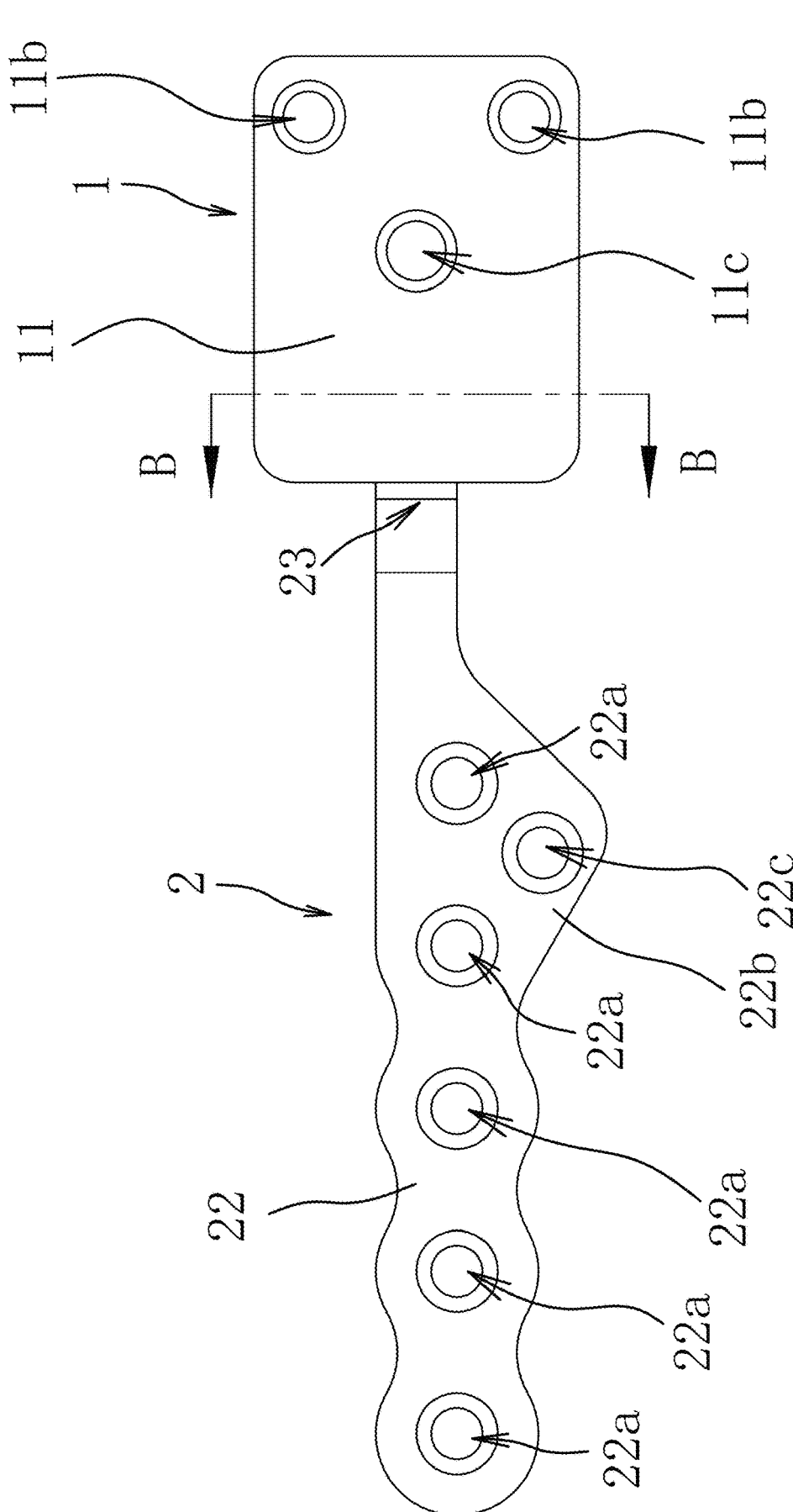
FIG. 11 is a top view of Embodiment II of an acromioclavicular steel plate assembly.
Figure 13:
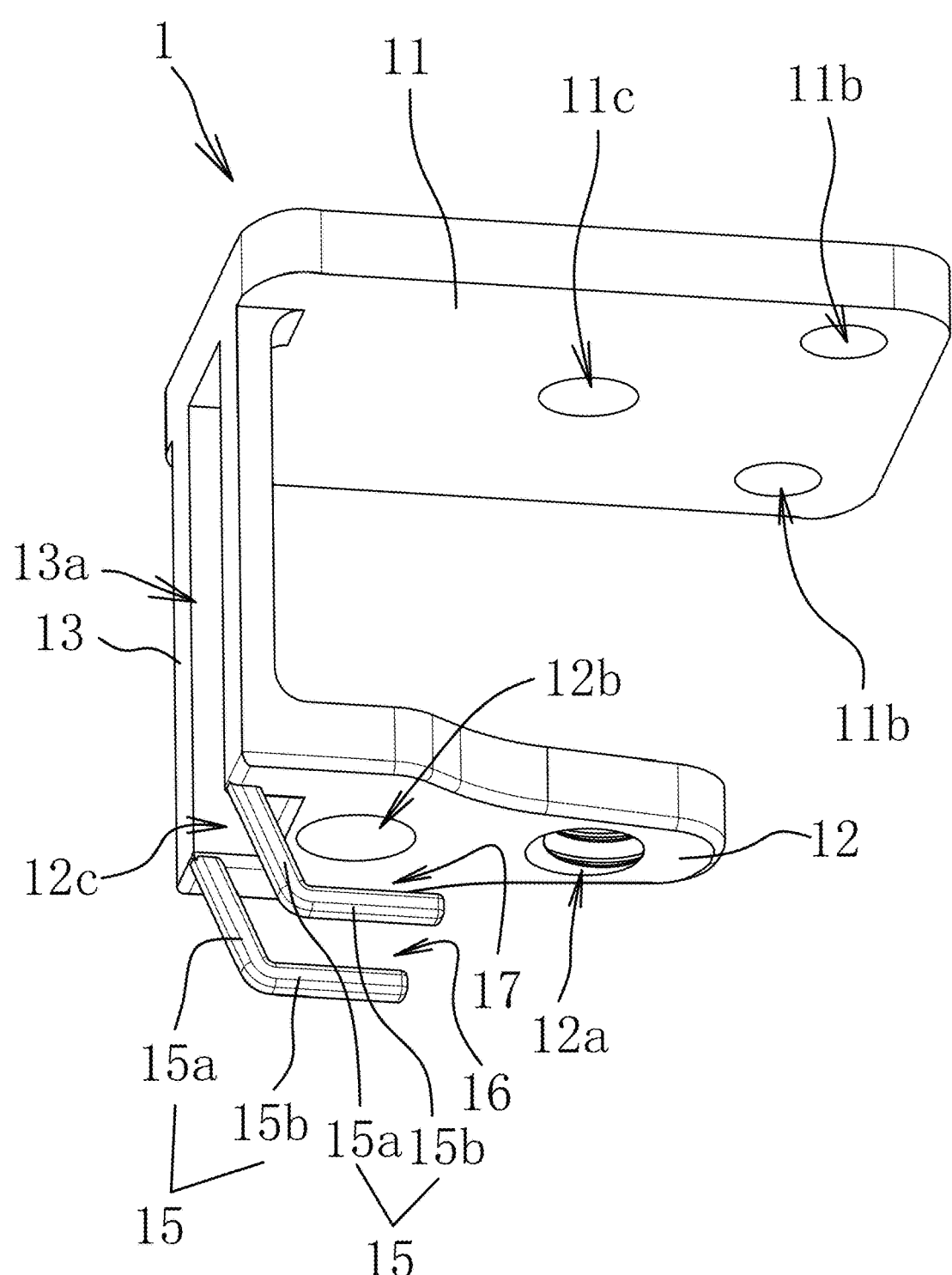
FIG. 13 is a perspective view showing a schematic structure of an acromion steel plate of Embodiment II of an acromioclavicular steel plate assembly.
Figure 14:
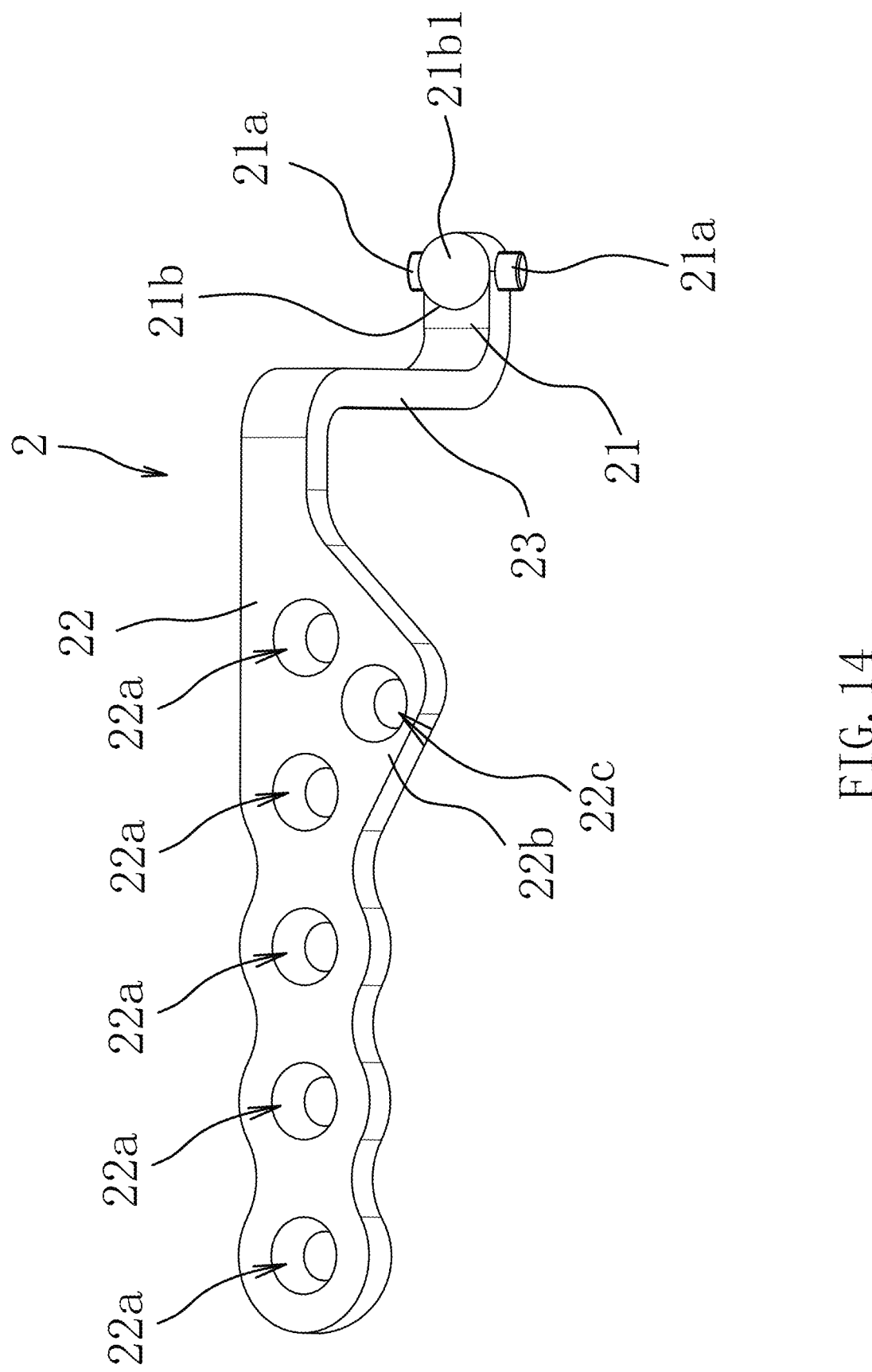
FIG. 14 is a perspective view showing a schematic structure of a clavicle steel plate of Embodiment II of an acromioclavicular steel plate assembly.

As shown in FIGS. 9, 10 and 13, other structures of the acromion steel plate 1 are basically the same as those of Embodiment I. As shown in FIGS. 9, 11, and 14, other structures of the clavicle steel plate 2 are basically the same as those of Embodiment I except that the extending portion 23 has a greater length.

As shown in FIGS. 8 and 9, when the acromion steel plate 1 is connected to the clavicle steel plate 2, the positioning head 21 is inclined to pass through the avoidance clearance 16 between the two limiting hooks 15, and then a normal state (without inclination) of the positioning head 21 is restored, such that the spherical hinge protrusion 21*b* is embedded into the bottom notch 12*b*. In this case, the limitation supporting portion 15*a* may block the limiting protrusions 21*a* of the positioning head 21, and hinged connection and limitation of the positioning head 21 and the acromion steel plate 1 are implemented. After the spherical hinge protrusion 21*b* is embedded into the bottom notch 12*b*, there are movable gaps between the extending portion 23 and the body 13, between the positioning head 21 and the limitation supporting portion 15*a*, between the positioning head 21 and the second fixing portion 11, and between the limiting protrusions 21*a* and the limiting hooks 15. The movable gaps do not need to be too large, so as to adapt to a movable range of 20° in all directions between the acromion steel plate 1 and the clavicle steel plate 2 for avoiding interference.

As shown in FIG. 10, the mounting structure of the acromioclavicular steel plate assembly on the clavicle 3 and the acromion 4 is the same as that of Embodiment I. When bone fracture has occurred, the clavicle 3 has upward thrust, the spherical hinge protrusion 21*b* of the positioning head 21 is tightly pressed on the second fixing portion 12 of the acromion steel plate 1, that is, the spherical hinge protrusion 21*b* abuts against a wall surface of the bottom notch 12*b*, and the acromion steel plate 1 is fixed on the acromion 4 of the scapula, such that an upward pulling force of a distal end of the clavicle 3 can be resisted. The hinged connection between the clavicle steel plate 2 and the acromion steel plate 1 is implemented by embedding the spherical hinge protrusion 21*b* into the bottom notch 12*b*. The transverse limitation of the acromion steel plate 1 on the clavicle steel plate 2 is implemented by arranging the limiting protrusions 21*a* and the limiting hooks 15. Therefore, when the acromioclavicular joint moves by 20° in all directions, the spherical hinge protrusion 21*b* can always make contact with a groove wall of the bottom notch 12*b* and rotate, such that the acromioclavicular joint can move normally and implement a normal acromioclavicular joint function. Furthermore, an upward dislocation force of the distal end of the clavicle 3 is converted into pressure on the lower bone surface of the acromion 4 of the scapula, and stable compression on the lower bone surface of the acromion 4 by the second fixing portion 12 of the U-shaped acromion steel plate 1 is used, such that damage to the upper bone surface or the lower bone surface caused by displacement of the acromion steel plate 1 due to instability of fixation and caused by large transverse displacement of the positioning head 21 is avoided, a risk that screws 5 are likely to be pulled off under the action of the dislocation force of the clavicle 3 when the acromion steel plate 1 only having the first fixing portion 11 is fixed on the upper bone surface of the acromion 4 only by the screws 5 is avoided, and use stability of the acromioclavicular steel plate assembly is improved.

The specific embodiments described herein are merely illustrative of the spirit of the present disclosure. A person skilled in the art to which the present disclosure pertains can make various modifications, additions, or similar substitutions to the specific embodiments described, without departing from the spirit and scope of the present disclosure defined by the appended claims.

REFERENCED PARTS 1 acromion steel plate
11 first fixing portion
11*a* notch
11*b* first fixing hole
11*c* second fixing hole
12 second fixing portion
12*a* third fixing hole
12*b* bottom notch
12*c* second avoidance gap
13 body
13*a* first avoidance gap
15 limiting hook
15*a* limitation supporting portion
15*b* limitation reinforcing portion
16 avoidance clearance
17 avoidance space
2 clavicle steel plate
21 positioning head
21*a* limiting protrusion
21*b* spherical hinge protrusion
21*b*1 spherical limiting surface
22 connecting portion
22*a* connecting hole
22*b* connection reinforcing portion
22*c* reinforcing hole
23 extending portion
3 clavicle
4 acromion
5 screw
6 reinforcing screw
H thickness of positioning head at spherical hinge protrusion
W total width of positioning head at two limiting protrusions
W0 width of first avoidance gap
W1 width of first fixing portion
W2 width of body
W3 width of avoidance clearance

What is claimed is:

1. An acromioclavicular steel plate assembly, comprising:
an acromion steel plate and a strip-shaped clavicle steel plate, wherein one end of the clavicle steel plate has a positioning head,
the acromion steel plate is an integrated steel component with three perpendicular acromion planes in a U shape, the three acromion planes being a body, a first fixing portion, and a second fixing portion,
the first fixing portion being on a first end of the body and perpendicular to the body,
the second fixing portion being on a second end of the body and perpendicular to the body,
a notch is arranged on a side surface of the first fixing portion facing the second fixing portion, a first avoidance gap is provided in the body in a length direction of the body,
two convex limiting protrusions are arranged on two side surfaces of the positioning head in a width direction of the clavicle steel plate respectively, a convex spherical hinge protrusion is arranged on one side surface of the positioning head in a thickness direction of the clavicle steel plate,
the positioning head is capable of passing through the first avoidance gap and embedding the spherical hinge protrusion into the notch, and
a total width W of the positioning head at the two limiting protrusions is greater than a width W0 of the first avoidance gap.

2. The acromioclavicular steel plate assembly as claimed in claim 1, wherein the two limiting protrusions are columnar, and two side surfaces of each of the two limiting protrusions in the thickness direction of the clavicle steel plate are cambered surfaces.

3. The acromioclavicular steel plate assembly as claimed in claim 1, wherein the spherical hinge protrusion is hemispherical, and the two limiting protrusions are arranged close to middle of the spherical hinge protrusion or close to a side of the spherical hinge protrusion facing the body in a length direction of the clavicle steel plate.

4. The acromioclavicular steel plate assembly as claimed in claim 3, wherein each of the two limiting protrusions is symmetrically arranged in a radial direction of the spherical hinge protrusion.

5. The acromioclavicular steel plate assembly as claimed in claim 1, wherein a thickness H of the positioning head at the spherical hinge protrusion is less than the width W0 of the first avoidance gap.

6. The acromioclavicular steel plate assembly as claimed in claim 1, wherein the clavicle steel plate is formed by three perpendicular clavicle planes in a Z shape, the three clavicle planes being the positioning head, a strip-shaped connecting portion capable of being connected to an upper bone surface on a clavicle, and an extending portion connected between the connecting portion and the positioning head, the extending portion and the connecting portion are perpendicularly arranged, and the extending portion and the spherical hinge protrusion are located on a same side surface of the positioning head.

7. The acromioclavicular steel plate assembly as claimed in claim 6, wherein one side surface of the connecting portion in the width direction of the clavicle steel plate has a convex connection reinforcing portion, and the connection reinforcing portion is provided with a reinforcing hole.

8. The acromioclavicular steel plate assembly as claimed in claim 1, wherein a width W2 of the body is less than a width W1 of the first fixing portion, the first avoidance gap penetrates the body in the length direction of the body, the second fixing portion is provided with a second avoidance gap in communication with the first avoidance gap, and the second avoidance gap penetrates the second fixing portion in the length direction of the body.

9. An acromioclavicular steel plate assembly, comprising an acromion steel plate and a strip-shaped clavicle steel plate, wherein one end of the clavicle steel plate has a positioning head, the acromion steel plate is an integrated steel component with three perpendicular acromion planes in a U shape, the three acromion planes being a body, a first fixing portion, and a second fixing portion, the first fixing portion being on a first end of the body and perpendicular to the body, the second fixing portion being on a second end of the body and perpendicular to the body, a bottom notch and two limiting hooks that are distributed in a width direction of the body are arranged on a side surface of the second fixing portion facing away from the first fixing portion, an avoidance clearance is formed between the two limiting hooks, two convex limiting protrusions are arranged on two side surfaces of the positioning head in a width direction of the clavicle steel plate respectively, a convex spherical hinge protrusion is arranged on one side surface of the positioning head in a thickness direction of the clavicle steel plate, the positioning head is capable of passing through the avoidance clearance and embedding the spherical hinge protrusion into the bottom notch, and a total width W of the positioning head at the two limiting protrusions is greater than a width W3 of the avoidance clearance.

10. The acromioclavicular steel plate assembly as claimed in claim 9, wherein each of the two limiting hooks is in a shape of an obtuse degree angled line, and comprises a limitation supporting portion arranged obliquely and a limitation reinforcing portion parallel to the second fixing portion.

11. The acromioclavicular steel plate assembly as claimed in claim 10, wherein an avoidance space allowing the positioning head to rotate is provided between the limitation reinforcing portion and the second fixing portion.

* * * * *